United States Patent [19]

Ginsberg et al.

[11] 4,276,051
[45] Jun. 30, 1981

[54] SYSTEM AND PROGRAM FOR CHEMICAL REACTION OBSERVATION WITH A MOVING PHOTOMETER

[75] Inventors: Guenter Ginsberg, Miami, Fla.; Thomas Horne, Harpenden, England

[73] Assignee: Coulter Electronics, Inc., Hialeah, Fla.

[21] Appl. No.: 115,734

[22] Filed: Jan. 28, 1980

[51] Int. Cl.³ .................. G01N 1/14; G01N 35/06
[52] U.S. Cl. ........................ 23/230 R; 364/497; 422/64; 422/67
[58] Field of Search ............... 422/63, 64, 65, 67; 364/497, 498; 73/425.4 R, 425.6; 23/230 R, 230 B

[56] References Cited

U.S. PATENT DOCUMENTS

| | | | |
|---|---|---|---|
| 3,192,968 | 7/1965 | Baruch et al. | 422/64 X |
| 3,193,358 | 7/1965 | Baruch | 422/64 |
| 3,723,066 | 3/1973 | Moran | 422/64 |
| 3,764,268 | 10/1973 | Kosowsky et al. | 422/64 |
| 4,058,367 | 11/1977 | Gilford | 422/67 |
| 4,155,978 | 5/1979 | Naono et al. | 422/64 |

*Primary Examiner*—Ronald Serwin
*Attorney, Agent, or Firm*—Silverman, Cass & Singer, Ltd.

[57] ABSTRACT

System and program for measuring progressively the absorbance changes of a large number of aliquots from a plurality of different samples in a continuous processing mode. A plurality of routine samples are maintained in an ordered sequence in a sample tray which may be moved to a first sample pick up position. Emergency samples (stats) and controls (standards) are positioned in a second plurality of auxiliary positions which may be moved to a second sample position. A first and second plurality of reagents are maintained, moved to respective reagent pick up positions, picked up, moved and dispensed in respective dispensing positions by respective single reagent dispensing arms in a similar manner to the sample operation. The chemical reaction is then monitored by photometer means preferably having a plurality of photometric detectors such that radiation passes through each of the cuvettes and the fluids therein during each cycle of the system. Just prior to the sample dispensing position the cuvette is cleaned and tested to ensure that all the previously added fluids have been removed prior to receiving a new sample. Any one sample may be tested with different reagents or reagent mixtures in different aliquots placed in separate cuvettes at each wavelength as desired. Each sample aliquot and reagent mixture may be measured to determine the rate of the chemical reaction and the equilibrium or end point of the reaction or both, if desired. The array of cuvettes is continuous, because it is replenished at the end of each sequence prior to the addition of the new sample.

57 Claims, 4 Drawing Figures

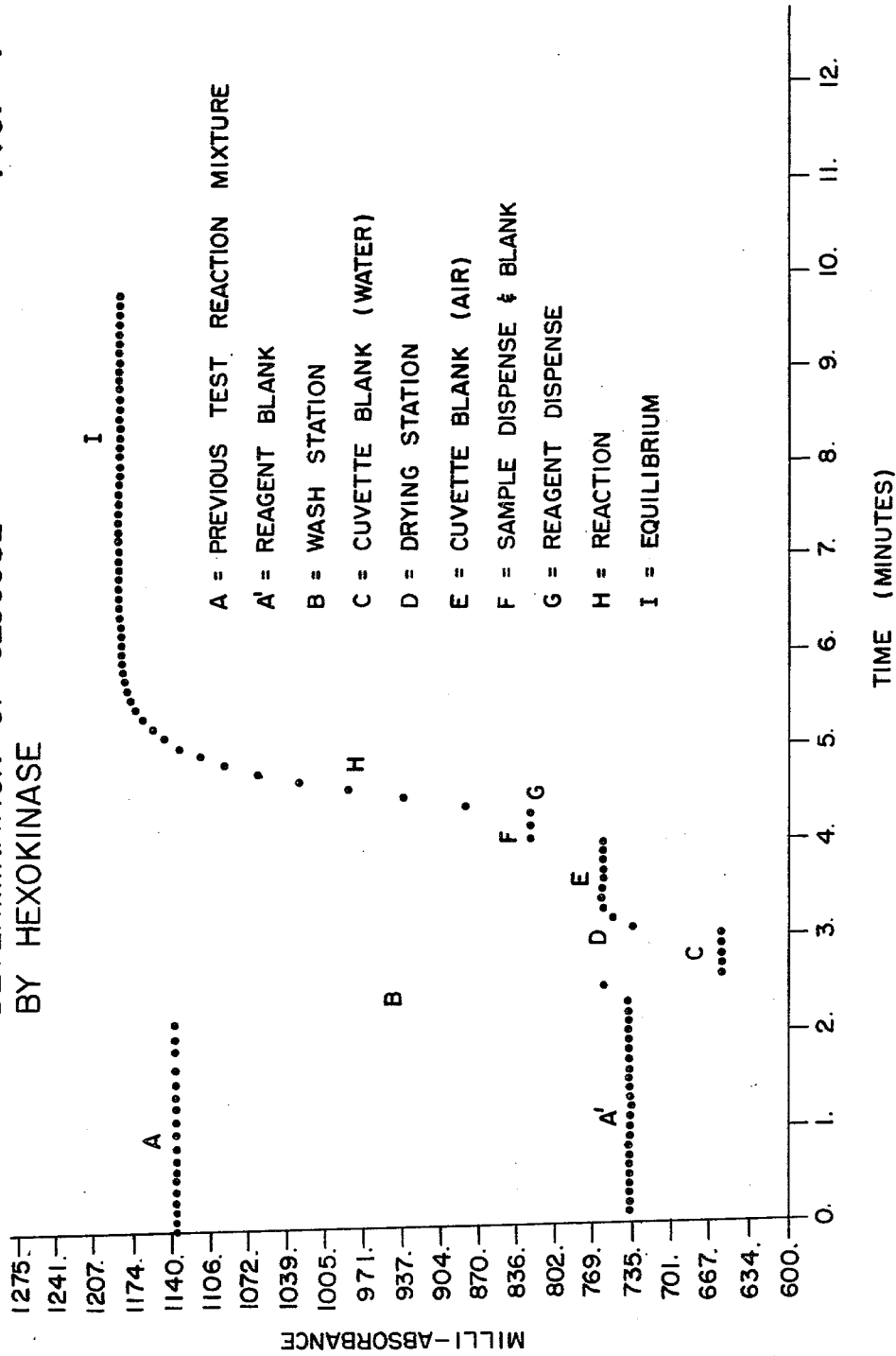

SYSTEM AND PROGRAM FOR CHEMICAL REACTION OBSERVATION WITH A MOVING PHOTOMETER

CROSS REFERENCE TO RELATED APPLICATIONS

This invention is related to the subject matter disclosed in the following copending and commonly assigned applications which are incorporated herein by reference:

Apparatus For Monitoring Chemical Reactions and Employing Moving Photometer Means, G. Ginsberg et al, Ser. No. 846,337, filed Oct. 28, 1977, now allowed.

Sample and Stat Feeding System and Sample Tray, G. Ginsberg et al, Ser. No. 115,924, filed Jan. 28, 1980.

Cuvette Washing Apparatus, B. Hodgins, Attorney Ser. No. 115,692, filed Jan. 28, 1980.

Fluid Transfer Mechanism, V. Drbal et al, Ser. No. 115,691, filed Jan. 28, 1980.

Probe Washer, B. Hodgins, Ser. No. 115,625, filed Jan. 28, 1980.

Variable Stop Syringe, B. Hodgins et al, Ser. No. 115,624, filed Jan. 28, 1980.

BACKGROUND OF THE INVENTION

The invention relates to a system and method of repeatedly observing the absorption of electro-magnetic radiation by a plurality of sample aliquots during a period of time. More particularly, this invention concerns the analyzing of a plurality of samples each of which may provide a single aliquot or plurality of aliquots which are subjected to chemical reactions with different reagents.

The term "aliquot" as employed herein is a noun meaning a portion of a sample. The term "auxiliary sample" is used herein to encompass control or standard samples, emergency-type samples, and similar fluids in distinction from a normally sequenced arrangement of patient samples. The system may measure kinetic reaction such as in enzyme analysis as well as end point or equilibrium conditions. Many chemical reactions requiring from a few seconds to several minutes may be initated substantially simultaneously and monitored to observe the progression of the reactions throughout a time period. The parameter measured is the absorbance of electromagnetic radiation of a particular wavelength or wavelengths by the analyte.

One disadvantage of prior art analyzing systems is the inability easily to handle an emergency situation as it arises without destroying the total sequence of operations of the system. In such systems the samples are laid out in a predetermined order to be tested, such as 1 through 50 with the identification and position of each of the samples being fixed. If during the sequencing of the samples and the tests run on the samples an emergency situation or stat test is desired, a position is robbed of its sample. The emergency situation or stat test is a sample which must be analyzed immediately and thus the programmed sequence of testing in progress must be interrupted. Each of these stat tests changes the programming of the tests and samples already in the programmed test sequence in the analyzer. Each change in the predetermined order or programming of the tests amd sample locations correctly must be entered and correlated so that the alteration of the sequencing is correctly noted in the system. This may result in the mismatching of a test and a sample resulting in an improper analysis related to a particular patient and all those following the mismatch in the sequence. It is extremely critical that a system accurately observe each sample reaction mixture being tested as will as have the flexibility to handle an emergency or stat situation should it arise during a sequence of testing without endangering the correct correlation of the test and samples already in the testing sequence.

A second problem encountered by the prior art devices is caused by dedicated reagent positions and typically a dedicated reagent dispensing mechanism for each position. In this case the array of cuvettes is segmented or divided into the number of positions required by the dedicated reagent positions. For example, 100 cuvette positions with 10 reagent positions results in samples from only 10 patients being tested without regard to the number of tests to be conducted on the sample from each patient. Patient No. 1 might require only one test, but all ten positions have to be alloted for that patient's sample in the device. Each of the nine empty positions may not be utilized so that the hundred position machine only is effective as a ten sample machine. If this problem is doubled by including ten second reagents, then the one hundred position machine would be divided in half again such that samples from only five patients could be analyzed at one time. This results in a great increase in elapsed time for a given throughput as well as a corresponding decrease in the efficiency of the operation.

SUMMARY OF THE INVENTION

The above and other disadvantages of prior art analyzing systems and techniques are overcome in accordance with the present invention by providing one pick up position for each of a plurality of samples, stat and blanks, first reagents and second reagents which are moved to the pick up position. A cuvette array sequentially is indexed to a single sample, stat and blank and one or more reagent dispensing positions. As employed herein, "index" is a verb which encompasses both stepping and continuous or smooth movement. Photometer means, preferably including a plurality of photometric detectors, continuously scan the array of cuvettes at a speed faster than the overall speed of the array. The photometer means preferably rotates continuously, scanning the cuvettes in each position whether or not a complete chemical reaction mixture is in the cuvette. Just prior to reaching the sample dispensing position the cuvettes are cleansed of the previously added fluids and tested to see whether they are clean and dry prior to receiving a new sample aliquot.

BRIEF DESCRIPTION OF THE DRAWINGS

FIG. 4 is a typical chart of values produced by testing of a sample in apparatus constructed in accordance with the invention.

DESCRIPTION OF THE PREFERRED EMBODIMENTS

Apparatus Subassemblies

Figure 1:
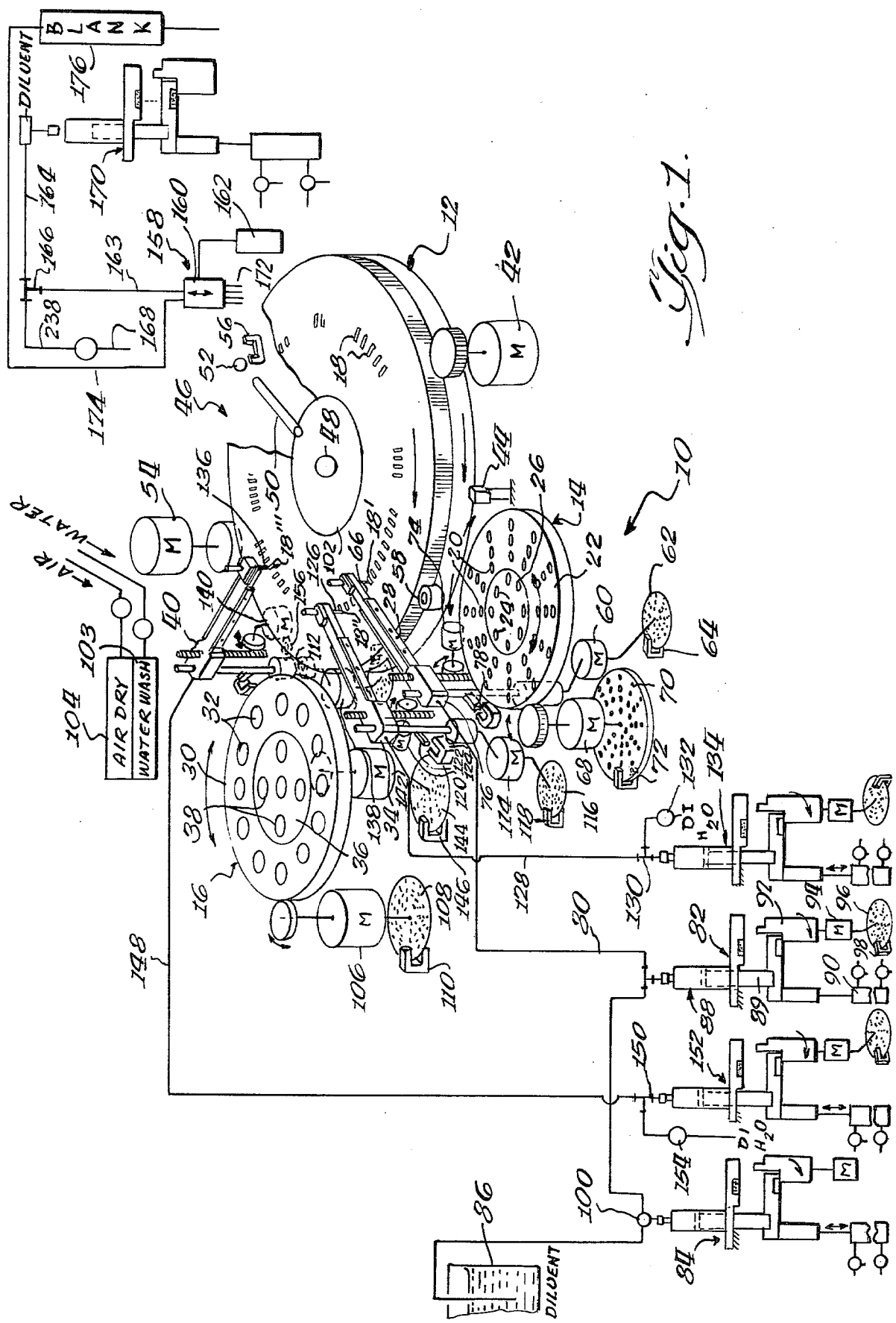
FIG. 1 is a diagramatic view of the apparatus of the invention showing the operational relationships between the various elements.

Referring now to FIG. 1, apparatus constructed in accordance with the invention is designated generally by the reference character 10. The major units of the apparatus or analyzer 10 include a cuvette disc or rotor 12, a sample tray or disc 14 and a reagent tray or disc 16. The cuvette rotor 12 includes a plurality of cuvettes or cuvette cavities 18 into which are dispensed samples, stats or blanks from the sample tray 14. The samples are contained in a plurality of sample cavities or cups 20 in a first outer section 22 of the sample tray 14. The stats and blanks are contained in a plurality of stat cavities or cups 24 in a second inner portion 26 of the sample tray 14. The samples, stats or blanks are picked up from the sample tray cavities, moved to and dispensed into the rotor cuvettes 18 by a sample dispensing arm 28.

The reagent tray 16 has an outer independently driven first reagent ring 30 having a plurality of reagent cavities or cups 32. Each cup contains a first reagent which is picked up from the cup and dispensed into the rotor cavities 18 by a first reagent dispensing arm 34. The reagent tray 16 includes an inner second reagent ring 36 having a plurality of second reagent cavities or cups 38. The second reagents are picked up from the cups 38 moved to and dispensed into the cavities 18 by a second reagent dispensing arm 40.

The cuvette disc 12 is rotated in an indexing movement by a motor 42. A sensor 44 reads a positional code (not shown) on the periphery of the rotor 12 to enable the analyzer to identify the particular cuvette at each location around the disc. Each of the cuvettes 18 is fixed in a specific angular position relative to the fixed location of the sensor 44 each time the code is read, which locates each cuvette relative to the position of the sensor 44 and therefore relative to the other analyzer mechanisms. For example, there may be a hundred and twenty cuvettes spaced circumferentially, preferably equiangularly around the rotor 12. The motor 42 is normally operated in a stepping mode, but also could be operated in a slowly and continuously rotating mode if desired.

The cuvettes 18 and the various reactions and other operations taking place therein are monitored by photometer means indicated generally at 46. The photometer means 46 include a source of light 48 which provides a beam that traverses an optical tube 50 to pass through a cuvette 18 and the liquids therein (if any) to be sensed by a photodetector 52. As the photometer means 46 rotates relative to the cuvette disc 12, each of the cuvettes and its contents will be scanned sequentially in the same manner. The photometer means 46 most conveniently are rotated continuously by a motor 54 by way of a conventional belt or gearing drive. The photometer 50 and photodetector 52 may be one of a plurality of photometers, such as eight, for example. At least one of the photometer units 50 and 52 may include an optical reader 56 which will read a conventional optical code (not shown) preceding each of the cuvettes 18 to identify the particular one of the cuvettes 18 being scanned by the photometer means 46. Each of the photometer means 46 could have a separate optical reader 56; however, the individual photometer units will be fixed angularly one relative to the other, such that identification of a cuvette 18 which any one photometer unit is scanning will, by definition, identify the respective cuvettes being scanned by each of the other photometer units. The results of the photometer readings are typically expressed in absorbance units as will be described with respect to FIG. 4. The operation of each of the major units or subassemblies 12, 14 and 16 will now be described in detail referring to FIGS. 1 and 2.

Cuvette Disc And Sample Tray Operation

One of the cuvettes 18 is moved into a sample dispensing position 18'. The sample dispensing arm 28 carries on its distal end a sample probe 66, which is utilized to pick up and to dispense sample aliquots. The arm 28 is shown lowered into the dispensing position with the probe 66 inserted into the cuvette at position 18'. The arm 28 would normally be in a rest position with the probe 66 removed from the cuvette 18, such as above a probe washer 58. The analyzer 10 has a predetermined sequence which determines which sample, stat or blank is to be dispensed into the cuvette at position 18'. The arm 28 first will be rotated by a motor 60 to a desired pick up location above one of the cavities 20 or 24. The location and control of the arm 28 by the motor 60 will be determined by a code wheel 62 which is read by an optical reader 64. When the reader 64 determines that the code wheel 62 is in the proper position the motor will be stopped with the dispensing arm 28 positioned over the proper location.

The analyzer 10 also will in the meantime have rotated the proper one of the cavities 20 or 24 into the pick up position defined by an arc of the probe 66 on the rotating arm 28. The disc 14 is rotated by a motor 68 which is controlled by a code wheel 70 read by an optical reader 72. The sample arm 28 is reciprocated vertically by a second motor 74. The vertical position of the arm may be sensed by an optical reader 76 which reads a vertical position tab 78 on the arm 28. The tab 78 and reader 76 are utilized by the analyzer to ensure the arm and probe 66 are in the lower position. Another reader (not shown) also may be utilized with each of the arms to ensure that the arm is in the up position, so that the probes will not be damaged when the arms, discs or trays are moved. The probe 66 is coupled by a line 80 to a multiple position sample syringe 82 and a multiple position diluent syringe 84 and to a source of diluent 86. The diluent may be distilled water.

Each of the multiple position syringes is essentially identical and only the first syringe 82 will be described in detail. The syringe 82 includes a syringe 88 and syringe plunger or piston 89, which is reciprocated between an upper completed dispensing position and a lower completed aspriating position by a pneumatic or hydraulic cylinder 90 in a conventional manner. The lower completed aspirating position is determined by a multiple stop 92, which has a plurality of stop positions which vary as the stop 92 is rotated by a motor 94. The positioning of the stop 92 and consequently the amount of fluid aspirated by the syringe 88 is determined by a code wheel 96 read by an optical reader 98. The analyzer 10 may preselect a predetermined amount of sample to be aspirated by the sample syringe 88, which is selected by rotating the multiple position stop 92 to the proper position as determined by the code wheel 96 and reader 98. Once the proper volume is selected and the sample probe 66 is inserted into the proper sample or stat vessel 20 or 24, the cylinder 90 is activated to draw the syringe plunger 89 into the lower position with-drawing or aspirating the predetermined amount of sample from the vessel in the sample tray 14.

The arm 28 then will be driven to the uppermost vertical position by the motor 74 and rotated by the motor 60 to a position over the cuvette in location 18' as determined by the code wheel 62 and reader 64. The arm 28 then is driven down into the cuvette by the motor 74 until the tab 78 is read by the optical reader 76. The sample syringe plunger 89 is driven to its uppermost position discharging into the cuvette the precise aliquot of sample that it had picked up from the sample tray 14. The sample aliquot is diluted with a predetermined amount of diluent by the second syringe 84, which has been selected by the analyzer 10 for the particular test aliquot. The syringe 84 will aspirate and dispense the diluent through a valve 100 from the source of diluent 86, operating as described for the sample syringe 82. When the sample aliquot has been dispensed, the syring 84 is activated with the valve 100 coupled to the line 80, to add the precise amount of diluent to the cuvette at position 18' where it may be stirred by an agitation motor 102 coupled to the probe 66. The diluted sample aliquot then is in the cuvette awaiting measurements of its absorbance by the photometer means 46 and the delivery of a first and second reagent, if necessary, from the first and second reagent dispensing arms 34 and 40. The reagents are dispensed into the cuvette when it has been rotated to their respective dispensing positions, 18" and 18'".

After the probe 66 has dispensed the sample and diluent and mixed them in the cuvette the motor 74 is again activated to raise the dispensing arm 28 to its uppermost traveling position. The motor 60 rotates the arm to a position above the probe washer or washing station 58. The motor 74 is activated to move the probe 66 down into the central opening of the washer 58 where the exterior of the probe is washed by an external water spray from a source 103 and by air directed in a stream above the water spray from an air supply 104. The connections to the washer 58 are not shown. At the same time, the inside of the probe 66 is flushed by a quantity of diluent which has been aspirated from the diluent supply 86 by the diluent syringe 84 through the valve 100. The valve 100 then is opened to the line 80 to dispense the diluent wash fluid through the inside of the probe 66 into a waste receptacle (not shown) connected to the probe washer 58 together with the external wash water from the wash supply 103. The water spray from the source 103 is then turned off while the air spray from the air supply 104 remains on to dry the outside of the probe 66. The air supply 104 is turned on at the same time as the water source 103 to ensure that the water flows to the waste receptacle to prevent a water aerosol from forming above the probe washer 58. The probe then is returned upward into its rest position by the motor 74 and is in position for its next operation.

Cuvette Disc And Reagent Sample Tray Operation

A. Primary Reagent

During this same period of time a cuvette in the first reagent dispensing location 18" will be receiving the first reagent from the first reagent dispensing arm 34. The reagent delivery operation is essentially the same as that described for the sample transfer from the sample tray 14 to the cuvette 18'. The first reagent ring 30 will be rotated by a motor 106 to move the proper reagent cup 32 into a pick up position for the dispensing arm 34 as determined by a code wheel 108 and reader 110. In a manner similar to the operation and action of the arm 28, the arm 34 will be rotated from its rest position over its probe washer 112 by a motor 114 controlled by a code wheel 116 and reader 118. The dispensing arm 34 is driven in its vertical travel by a motor 120 and similarly includes a tab 122 read by a reader 124 to determine when it is in the pick up location. The arm 34 includes a probe 126 which is coupled to a line 128. The line 128 is coupled through a valve 130 to a source of deionized (DI) water 132 and a first reagent syringe 134.

The syringe 134 operates in a manner similar to the operation of the syringe 82. The analyzer 10 selects the appropriate stop for the syringe 134 and the proper amount of first reagent is aspirated from the vessel 32 in the pick up location. The arm 34 is then driven upwardly to its upper position and rotated until it is above the cuvette located in the position 18" as determined by the code wheel and the reader 118. The arm 34 is then driven downwardly to insert the probe 126 into the cuvette at which point the syringe 134 will be activated to dispense the first reagent aliquot into the cuvette where it is mixed by the probe 126. The probe 126 then is removed from the cuvette and inserted into the probe washer 112 where the outside of the probe 126 is washed in the same manner as described for the probe 66. The inside of the probe is washed by a quantity of water, preferably deionized (DI) water, from the source 132 which has been aspirated by the syringe 134 through the valve 130. The DI water is dispensed through the line 128 and probe 126 into the probe washer 112. The arm 34 is then driven upwardly to its rest position over the probe washer 112 ready for its next operation.

B. Second Reagent

When the cuvette arrives at the second reagent dispensing location 18'" a second reagent may be added in a manner similar to the delivery of the first reagent. The dispensing arm 40 includes a probe 136 which will be inserted into the cuvette at the position 18'" to dispense and mix the second reagent in each cuvette 18 where a second reagent is required for the particular test reaction to be observed. The arm 40 is rotated by a motor 138 and is driven in its vertical motion by a motor 140. The probe 136 is moved into a second aspirating position over the second reagent ring 36, which is independently located by a drive motor 142 with its associated code wheel 144 and reader 146. The probe 136 aspirates the proper amount of the second reagent from the proper reagent cup 38 located in the pick up position, which also is on an arc of the probe 136 on the rotating arm 40.

The dispensing arm 40 is coupled by a line 148 to a valve 150 which couples the line 148 either to a second reagent syringe 152 or a source of deionized water 154. In a similar manner to the syringe 82 the variable stop syringe 152 has been activated to select the proper volume before the syringe plunger is driven to the aspirated position to ensure that the syringe will aspirate the proper amount of the reagent from the vessel 38. The arm 40 is then moved into the uppermost rotating position and rotated to the cuvette 18'" where it is driven downwardly into the cuvette 18 at the dispensing position 18'". The syringe 152 then is operated to dispense the reagent aliquot which has been picked up into the cuvette where it again is mixed by oscillating the probe 136.

The arm 40 is then raised back to the rotating position and rotated to a probe washer 156. The probe 136 is driven downwardly into the probe washer 156 where it is externally washed by sprays from the water and air supplies 103 and 104 and then dried by the air spray. The probe 136 will be flushed internally by the syringe 152. The syringe 152 aspirates a predetermined amount of deionized water from the source 154 through the valve 150 and then is coupled to the line 148 to dispense the water to flush the internal portion of the probe 136. The analyzer 10 monitors the reaction in each vessel 18 either for a rate of reaction test or for an end point condition or for both, if desired.

Wash Station Operation

Each cuvette 18 is moved in a rotary motion on the cuvette disc 12 by the motor 42 and reaches a wash station 158 after the reactions have been monitored for a sufficient time period to obtain the information of interest. The wash station includes a wash stand 160 which is driven downwardly into the cuvettes by a pneumatic or hydraulic cylinder 162 or by a motor. The wash stand 160 is coupled by a dual line or lines 163 to a valve 166. A syringe 170 provides wash fluid, such as diluent, through a line 164 to the valve 166. The wash fluid flows through one side of the dual line 163 to one of a plurality of probes 172. This scavenge and wash probe will include a water entry port or ports (not shown) and a drying or vacuum port (not shown) to exhaust the wash fluid and reaction mixture through the other side of the dual line 163 to the valve 166 and through a line 238 to a source of vacuum 168 and then to a drain. The wash fluid and vacuum will be applied to the cuvette simultaneously and then the vacuum source will be left on to dry the cuvette after the wash fluid is expended. The wash stand typically may have a plurality of probes 172 which simultaneously are inserted into different ones of the cuvettes 18. The probes 172 may include a temperature probe, wash probes, nozzles and drying probes as desired.

One of the probes 172 will be coupled to a line 174 and to a source of blanking solution 176. The blanking solution, preferably diluent, will be inserted into the cuvette 18 after the cuvette has been washed so that the photometer means 46 may read the blank liquid to see if the cuvette has been cleaned satisfactorily. This is accomplished by comparing the reading of the photometer means 46 at the optical wavelength that the cuvette 18 was read prior to initiating the just completed test. If the absorbance of the cuvette 18 is within predetermined limits of the previous blank absorbance value, then the cuvette will be utilized in the next series of tests. If the cuvette fails the test, the analyzer will ignore the cuvette and will not dispense any sample or reagent into that cuvette, at least until it has gone through the wash cycle again. Once the blank solution has been tested in the wash stand, a further step or steps of the cuvette will bring it to another one of the probes 172, which will remove the blank solution from the cuvette to prepare it for the next sample insertion. This probe also may dry the cuvette at the same time or the cuvette drying may be provided in a further location with a separate probe.

The spacing of the transfer assemblies 28, 34 and 40, as well as the sample tray 14, reagent tray 16 and the wash station 158 are shown in the order of sequence of events, but are not shown at any precise location. For example, the wash station 158 preferably would be located very close to the sample dispensing station 18'. Each of the stations 18', 18" and 18''' will be located as close together as feasible allowing for any initial reactions to occur between 18" and 18'''. The spacing is not critical, but ensures that a complete sample and reagent mixture will be observed the optimum time as the rotor 12 is indexed between the second reagent dispensing position 18''' and the wash station 158.

Hydraulic And Pneumatic Operations

Figure 2:
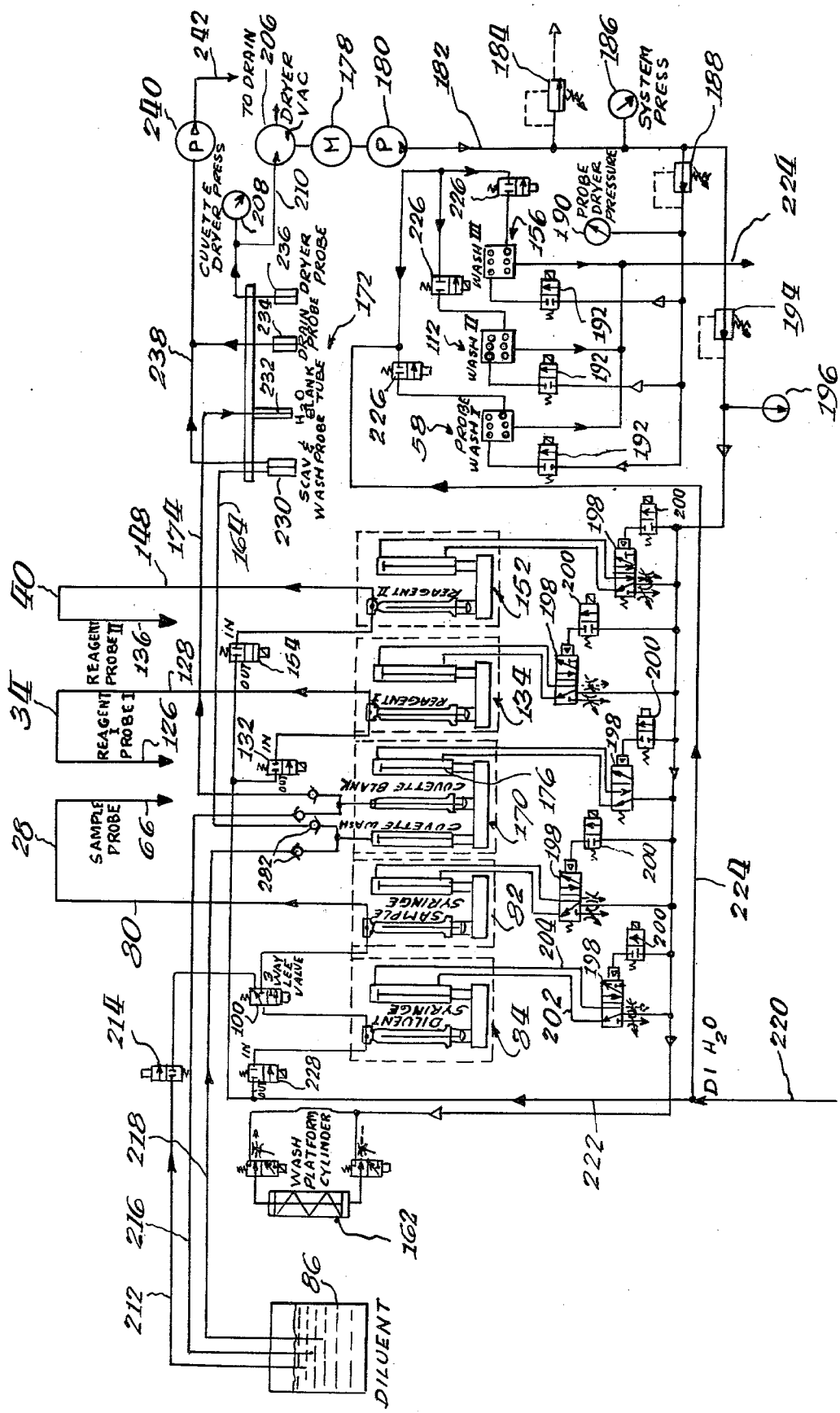
FIG. 2 is a hydraulic and pneumatic schematic diagram of the invention.

Referring now to FIG. 2, the hydraulic and pneumatic schematic of the analyzer 10 is illustrated. The functions illustrated in FIG. 2 corresponding to those in FIG. 1 are shown with the same reference numerals. Pneumatic pressure is provided by a motor 178 driving a pump 180 which is coupled through a line 182 to a relief valve 184. The relief valve 184 protects the analyzer 10 from a malfunction in the motor or pump. The line 182 also is coupled to a gauge 186 to display the pressure output of the pump 180. The line 182 is coupled through a regulator valve 188 to the wash probes 58, 112 and 156 with the pressure output from the valve 188 being displayed by a gauge 190. Each of the probe washers is coupled to the regulator valve 188 by an independently operated valve 192. The valves 192 may be operated simultaneously assuming that the three probes 28, 34 and 40 are being operated simultaneously. It is not necessary to operate the respective probe washers 58, 112 and 156 if their respective probes 28, 34 and 40 were not utilized for a particular test.

The line 182 also is coupled through a regulator valve 194 to operate the pneumatic cylinders for the syringes 82, 84, 134, 152 and 170 as well as the drive cylinder 162 for the wash stand or platform 160. The regulated pneumatic output from the valve 194 is displayed by a gauge 196. Each of the syringes includes a pair of control valves 198 and 200 to operate the drive cylinders. The valve 198 is a multiple position valve which is operated by the pilot valve 200. In operation, for example with the syringe 84, the output of the regulator valve 194 is coupled either to a line 202 or a line 204 to reciprocate the syringe up or down, respectively.

The motor 178 also is connected to a final drier or vacuum pump 206 with the pressure output displayed by a gauge 208. The drier pump 206 is connected directly by a line 210 to a drier probe which is one of the plurality of probes 172 in the wash stand 160. The operation of the drier probe will be discussed in its proper sequence along with the rest of the probes 172 on the wash stand 160.

The diluent supply 86 is coupled via a line 212 to and through an isolation valve 214 to the valve 100. The isolation valve 214 is utilized, because of the precision necessary in the system to prevent the fluid from moving in the line when the valve 100 is switched between the diluent supply 86 and the sample probe 66. The valve 214 could be eliminated merely by equalizing the hydraulic pressures, between the sample probe 66 and the diluent source 86 by stationing the diluent at substantially the same fluid level as the sample probe when the valve 100 is operated.

The diluent is supplied through a second line 216 to the syringe 170. From the syringe 170 it is coupled via a line 174 to the blanking fluid addition nozzle in the wash stand 160. The diluent source 86 is coupled via a third line 218 to the syringe 170 and from the syringe 170 through the lines 163 and 164 to the first wash probe in the wash stand 160. In this case, the diluent source 86 replaces the blank source 176 with the blank solution being provided by the diluent 86. If a different blanking solution was desired, the line 218 merely would be coupled to the separate source 176 as illustrated in FIG. 1.

A source of deionized (DI) water 220 is coupled via a line 222 to the syringes 84, 134 and 152. The source 220 is coupled through a second line 224 to the probe washers 58, 112 and 156, through a plurality of valves 226 which may be operated simultaneously or independently in a manner similar to that described for the valves 192. The source 220 is coupled to the syringe 84 through a valve 228, which is utilized to prime the syringe 84. The deionized water supplied through the valves 132 and 154 is utilized to internally flush the reagent probes 126 and 136 of the dispensing arms 34 and 40. The deionized water is also utilized to prime the probes 126 and 136.

In operation, the wash stand 160 may include among its plurality of probes 172 and a first scavenge and wash probe 230, a blank tube or nozzle 232, a drain probe 234 and a drier probe 236. The scavenger probe 230 and the drain probe 234 preferably are coupled via a line 238 to a separate scavenging pump 240. The pump 240 preferably would be a bellows-type pump which could remove any matter left in the cuvettes 18 without doing damage to the pump and which would then expel the matter removed from the cuvettes via a line 242 to a drain. Each of the probe washers 58, 112 and 156 would also have their output connected to the drain via a line 244.

In the sequential operation, the cuvette 18 first would be positioned in the wash stand 160 at the scavenger probe 230 which simultaneously would wash and remove by suction the expended sample and reagent and other matter from the cuvette. The wash fluid flows down between the probe 230 and the walls of the cuvette and is removed through the bottom of the probe by the suction applied through the line 238. The cuvette then would be moved to the blank insertion position 232 where the diluent or other blanking solution would be added via the line 174. The blank value of the solution and cuvette then would be read by the photometer means 46 between the blank insertion position 232 and a drain probe position 234. The drain probe 234 then would remove all the moisture from the cuvette 18. The last position 236 would complete the drying of the cuvette 18 preparatory to having another sample aliquot added to it at the sample position 18' to initiate the next cycle in the continuous testing sequence. Alternately, the blank insertion nozzle 232 could be replaced with a wash probe similar to the probe 230 with the fluid inserted from the bottom of the probe and the vacuum at the top. A sufficient amount of wash fluid is left in the cuvette to serve as the blank solution. A single drain and dryer probe also could be utilized instead of the two separate probes 234 and 236.

Timing Of One Sequence Of Operations

Figure 3:
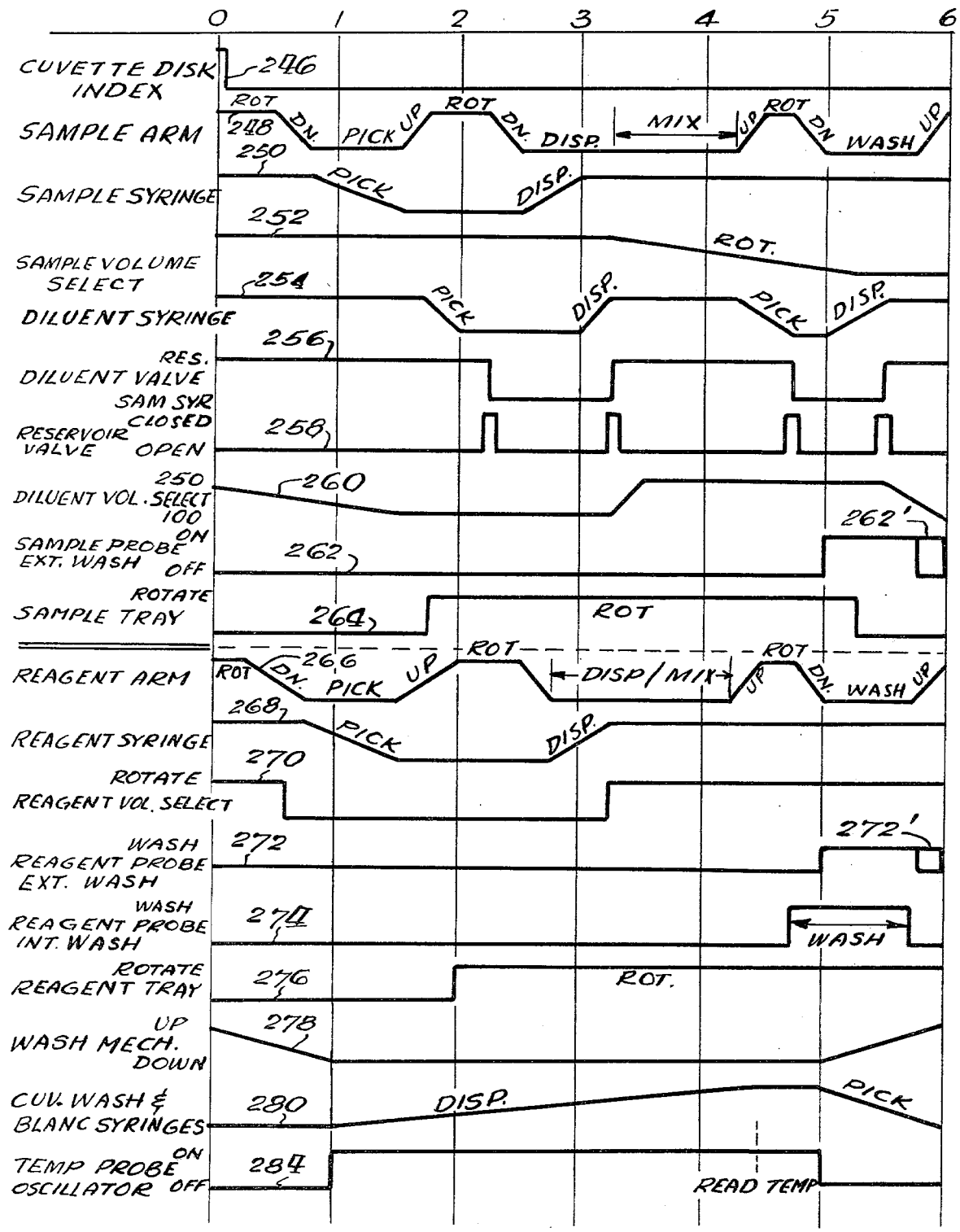
FIG. 3 is a timing diagram for one cycle or operation sequence of the invention.

Referring now to FIG. 3, the timing of the sequence of operations of the analyzer 10, shown diagrammatically in FIGS. 1 and 2, will be discussed. The indexing of the cuvette disc 12 is shown by a first wave form 246. The operations of the sample arm 28 are illustrated by a wave form 248. In each dwell period, the sample arm 28 (proceeding from left to right) will first rotate (ROT) from its rest position until it is above the proper pick up position. It then will be driven down (DN) until it is in a proper sample fluid where it will aspirate or pick up (PICK) the proper sample volume following which it will be driven up to its rotating position. It then will be rotated to the dispensing position 18', and driven down into one of the cuvettes 18, dispense the sample and diluent and then mix the sample and diluent for approximately one second. The probe then will be driven up and rotated to a position above the probe washer 58, driven down into the probe washer 58, washed internally and externally and then it will be returned to its rest position above the probe washer 58, ready for the next cycle.

The operations of the sample syringe 82 are shown by a wave form 250. The syringe is activated in the fully discharged position and aspirates the sample aliquot, preferably at a fixed rate, once the sample arm has driven its probe into the sample fluid and holds the sample aliquot while the sample arm 28 is raised and rotated to the dispensing position 18'. The sample syringe 82 then will be activated to expel or dispense (DISP) the sample aliquot into the cuvette prior to the mixing operation of the sample arm 28.

The sample volume selection by the analyzer 10 is shown by a wave form 252. The selection is accomplished by the adjustable stop 92, motor 94, code wheel 96 and the reader 98 in FIG. 1. Once the sample syringe 82 has completed the dispensing operation (wave form 250), the analyzer will select the new sample volume and then rotate the variable stop 92 to the next volume selection position prior to the next operation of the syringe 82.

The operation of the diluent syringe 84 is illustrated by a wave form 254. The diluent syringe is coupled to the same line 80 as the sample syringe 82 by the valve 100 and must aspirate or pick up the diluent prior to dispensing of the diluent, preferably just before the diluent is dispensed. The diluent then is dispensed into the cuvette prior or during the mixing action of the sample arm, but before the termination of the mixing. The diluent syringe 84 is then operated again to pick up a second diluent volume, generally greater than the aliquot diluent volume, which is dispensed when the probe is in the probe wash 58 to internally wash the sample probe 66. The diluent syringe operates to provide the diluent to each sample aliquot and to internally wash the sample probe following each sampling operation.

The operation of the diluent valve 100 is illustrated by a wave form 256. The diluent valve 100 is normally in a reservoir position coupled to the diluent source 86 and closed to the sample syringe 82 and probe 66. Following the aspiration of the diluent by the diluent syringe 84, the valve 100 is switched to its sample syringe position coupling it with the sample syringe 82 and the sample probe 66 and closing it to the diluent source 86. The sample aliquot in the probe 66 and the diluent volume will be dispensed by the dispensing operation of the sample syringe 82. The volume of diluent following the sample aliquot pushes and washes the sample aliquot from the inside of the probe 66 and mixes with it in the cuvette. If necessary, the sample aliquot and diluent will be mixed by the mixing action of the sample probe 66. The valve 100 then will be switched back to the reservoir or source 86 so that the diluent syringe 84 may aspirate the amount of fluid necessary to internally wash the sample probe 66 once it has reached the wash position. When the sample probe has reached the wash position in the probe washer 58, the valve 100 will be switched from the diluent source 86 to the probe 66 so the diluent syringe 84 may discharge the wash water through the probe 66. The valve 100 then will be switched back to its reservoir position ready for the next sampling operation.

The operation of the reservoir or isolation valve 214 is illustrated by a wave form 258. The valve is maintained normally in the open position, but is closed just before and opened just after the diluent valve 100 switches between the reservoir 86 and the sample syringe 82 to maintain the precise volume picked up without hydraulic leakage or siphoning between the sample probe 66 and the diluent source 86. As previously discussed, this could be eliminated by placing the intakes of the source of diluent 86 and the sample probe 66 at essentially the same height.

The volume selection of the diluent syringe 84 is shown by a wave form 260. The variable stop will be rotated to the predetermined volume necessary to provide the correct dilution of the sample prior to aspirating the sample aliquot as shown by the wave form 254. This volume typically will be considerably less than the volume utilized to wash the internal portion of the sample probe 66. The volume selected is changed between the diluent dispense and the probe wash operations and preferably will be greater for aspirating the amount of diluent necessary to wash the inside of the probe 66 when it is in the probe wash 58. If these volumes were designed to be the same this operation could be deleted and the diluent syringe 84 would have a fixed stop.

The operation of the sample probe wash 58 is shown by a wave form 262, which illustrates that the external wash of water and air on the probe wash 58 is turned on after the probe is moved into the central aperture in the probe wash 58. The water is turned off as the probe 66 is removed from the probe wash 58. The external air spray will continue as the sample probe 66 is removed from the probe wash 58 as shown by wave form 262'. The internal wash will be terminated prior to the probe 66 being removed from the probe wash 58 so that the outside of the probe will be dried by the air spray, but the probe will not spray diluent outside of the probe washer 58.

The movement of the sample tray 14 is shown by a wave form 264. The sample tray is in its rest position sometime before the sample arm 28 reaches the sample pick up position and stays in the rest position until the sample arm 66 has been removed from the tray cavity. The sample tray 14 then will be rotated to be ready for the next sample or blank aliquot to be picked up as determined by the number of tests to be run on the sample. The sample tray 14 may stay in its position for several stepping movements of the rotor 12, since a plurality of tests may be run on separate aliquots of any one of the samples located in the sample disc 14. Therefore, this operation only takes place when it is necessary to move to a new sample or stat into the sampling position. Further, although only one wave form 264 is shown there would be a second wave form if the sample and stat ring 26 is moved separately from the outer ring 22, in the same manner as the two separate rings of the reagent tray 16.

The operation of one of the reagent arms 34 or 40 is shown by a wave form 266. Each of the reagent dispensing arms 34 and 40 and their related assemblies preferably would have identical or substantially identical wave forms, such that the discussion of one wave form will suffice to explain the operation of both. It should be noted however, that in some instances the test being run on the sample aliquot in the cuvette 18 will only utilize one reagent and therefore one of the arms 34 or 40 would not be operated when that cuvette is in the respective dispensing position. The operations of the arm 34 are very similar to those of the sample arm 28. The reagent arm 34 will start from a rest position above the probe washer 112, be rotated to one of the first reagent cavities 32, be driven downwardly into the cavity to pick up the reagent, be driven up and rotated to its dispensing location at the cuvette 18''. The arm then will be driven down into the cuvette 18'', the reagent dispensed and the probe oscillated or otherwise moved so that the probe 126 will mix the reagent and the sample aliquot mixture, then moved upwardly, rotated to the wash position above the probe washer 112, driven downwardly so the probe 126 is inserted into the center of the probe washer 112, washed and then be driven upwardly back to its rotating and rest position above the probe washer 112.

The operations of the reagent syringe 134 during the cycle are shown by wave form 268. The piston of the reagent syringe 134 will be in its rest or fully dispensed position and will aspirate the reagent when the reagent arm 34 is in the cavity 32 in the pick up position. The piston is maintained in the fully aspirated position until the probe 126 has been inserted into the cuvette at the location 18''. The piston of the syringe 134 then will be driven to its completely dispensed position to dispense the reagent into the cuvette as the reagent probe 126 is oscillated to mix the fluids. The reagent syringe 134 is returned to its rest position until the next cycle. It is of course possible to select a test such that the reagent arm 34 would not be operated and the reagent arm 40 only would be operated. Furthermore, at the loss of throughput of the machine one of the arms 34 or 40 could select both the first and second reagents and provide both functions at one location. In that case, the reagent tray 16 could be a unitary tray as shown for the sample tray 14 and would not need the separate drives for the internal and external rings, although they could be maintained if desired.

The selection of the proper volume of the reagent syringe 134 is illustrated by a wave form 270. The wave form illustrates that the volume is selected just prior to the aspiration of the reagent; however, the variable stop may be rotated at any time in the cycle so long as it is in the selected position prior to the reagent probe 126 picking up the reagent as shown by the wave form 268.

The operation of the reagent probe wash 112 is illustrated by a wave form 272. The probe wash water and air will be turned on after the probe 126 is inserted into the open throat of the wash where it will be externally sprayed. The water will be turned off before the air as previously described. The wash normally is maintained in the off position with no water or air flow.

The internal probe wash operation for the probe 126 from the line 220 through the valve 132 is illustrated by a wave form 274. The internal wash may be operated when the probe 126 is positioned above the probe wash 112 and as it is driven into and out of the probe washer 112, only ensuring that fluid is not splashed outside of the washer 112.

The selection of the proper reagent container 32 on the first reagent ring 30 is illustrated by a wave form 276. The ring 30 is rotated prior to the probe 126 entering the container 32 located at the pick up location and will be maintained in that position until the proper volume of reagent has been aspirated by the probe 126 and the probe has been removed from the vessel or container 32. The ring 30 then will be rotated again, if necessary, to select the next reagent for the next sample aliquot which will reach the cuvette position 18" in the next cycle.

The operation of the wash stand or mechanism 160 is illustrated by a wave form 278. The wash stand 160 will be driven downwardly so that the plurality of probes 172 is each inserted into a separate cuvette 18 to accomplish their individual functions after each index of the disc 12. The wash mechanism 160 then will be driven upwardly before the disc 12 again is rotated. Each of the probes preferably will be operating substantially simultaneously to perform their functions.

The operation of the cuvette wash and blank syringe 170 is illustrated by a wave form 280. The syringe 170 will have aspirated in the previous cycle and then will dispense the required volume into the cuvette 18 to be washed, preferably over a substantial portion of the cycle to provide the greatest washing action possible for the insides of the just utilized cuvette 18. Referring to FIG. 2, a plurality of check valves 282 may be seen which automatically connect and disconnect the syringe 170 from the diluent lines 216 and 218 to the dispensing lines 164 for the wash probe 230 and 174 for the blank nozzle 232. The syringe 170 is operated first in the aspirate and then in the dispense mode. Therefore, at the end of the cycle the syringe 170 automatically will aspirate and draw in the proper amount of fluid into both the wash syringe and the blank syringe 176 ready for the next cycle.

One of the probes 172 of the wash stand may be a temperature probe to measure the temperature of the reaction mixture at the end of the cycle, if desired. In this case, it is convenient to oscillate the probe before measuring the temperature to reach an equilibrium state between the probe and the mixture and to overcome any thermal barriers to receive a quick and accurate check of the temperature of the reaction mixture. The operation of the temperature probe is illustrated by a wave form 284 which shows the oscillator being activated when the wash mechanism has been lowered into the cuvette 18 and the temperature being read at the end of the rest position in the cuvette 18. The oscillator is turned off as the wash mechanism is removed from the cuvette 18 to prevent splashing by the probe or other contamination of the analyzer. The temperature probe is not illustrated on FIG. 2, but would be situated on the stand 160 such that it measures the temperature of the reaction mixture in the cuvette 18 prior to reaching the position of the scavenge and wash probe 230.

To operate the analyzer 10, the control solutions and any stat or emergency samples would be placed in the cavities or cups 24. The controls are placed into the appropriate frequency of cuvettes 18, such as every tenth cuvette, without interrupting any of the sequencing of the other operations of the machine. Since the analyzer maintains a record of which sample is in each location and locates each position with the code wheel 70 and reader 72, there is no interruption of the sequencing of the sample tests which would disrupt the operation of the analyzer 10. The controls are used to check that the analyzer is operating correctly. Thus, any time an emergency or other type of situation of that type arises, the emergency sample may be put into the ring 26 in any appropriate position and the sample probe will pick it up on the next cycle.

One of the cavities 24 may be used for a microstat or pre-mixed stat which will be operated on substantially the same as previously described for a regular sample. The microstat if it has sufficient volume may be picked up, dispensed and diluted as previously described. If desired, the microstat may be pre-diluted in which case the sample syringe 82 will be disabled and the diluent syringe 84 will be operated with the valve 100 connected to line 80 to pick up the microstat in the probe 66.

The diluent syringe 84 is used to pick up the pre-diluted microstat since a larger volume aliquot will be picked up by the sample syringe 82, than in the case of the normal sample aliquot. The diluent syringe 84 will be activated to dispense the pre-diluted microstat when the probe 66 has reached the dispensing position in the cuvette 18.

Determination Of Glucose By Hexokinase

A specific example of the operation of apparatus constructed and operated in accordance with the invention, is illustrated in FIG. 4. The specific example being a determination of glucose by hexokinase. In the specific example, the timing of FIG. 3 is utilized with each operation sequence or cycle being six seconds and the reaction being observed or monitored only by one of the photometer units at the appropriate wavelength. The horizontal scale is time in minutes and the vertical scale is a measurement of absorbance units as determined by the photometer means 46.

The time scale of O on the chart represents a time just prior to the cuvette reaching the wash station 158 with the results of the previous reaction mixture shown at A. The reagent blank for the determination of glucose must be determined prior to testing the samples and is illustrated at A'. This reagent blank would typically be determined prior to the start up of the sequence of testing for each of the reagents in the analyzer 10. Therefore the portion shown at A' is a stored value which would not be determined in the normal sequence of testing. The reagent blank value is important, because it must be known to normalize the end point determination to an absolute value by eliminating the reagent blank from the end reaction reading shown at I. The end reading includes the blank value for the reagent or reagents included in the reaction mixture. The analyzer 10 would record the value or reading of the mixture A and then immediately move into the wash station as shown at B.

The readings at the wash station are shown by B with the measurements being due to the light passing around the wash probe. If the wash probe completely filled the cuvette the readings would be at a higher levels since most of the light would be eliminated.

Following the cuvette air blank shown at E, the sample is dispensed into the cuvette at the location 18' and the sample blank F is then obtained between the location 18' and the location 18". At G the position 18" has been reached and the first reagent (in this example) is dispensed into and mixed with the sample aliquot. At this point the reaction curve starts as shown at H. The rate of change of the reaction is shown by the rapid increase in the curve H and depending on the test may be the result desired to be determined or the equilibrium or end point position shown at I may be the desired result, or both. In this case only a first reagent has been shown as being dispensed; however, there would be a further dispensing of the second reagent at the position 18''' if the particular test requires such a second reagent. The cuvette disc 12 is indexed such that at the end of a complete operation sequence, the wash station 158 again will be reached and passed by the cuvette and the sequence will be initiated again with a new sample being dispensed. In that case the cuvette blanks, shown at C and E, will be taken both at the old wavelength to determine if the cuvette has been cleaned and dried and at the new test wavelength to provide the normalizing factor for the new test. At the end of the reaction the final value will of course have the blank values eliminated from the equilibrium value by the analyzer 10.

One specific example of the analyzer 10 includes one hundred and twenty cuvettes 18 in the rotor 12. Each cycle or dwell time between indexing is substantially six seconds, and there are one hundred steps between the sample dispensing position 18' and the initial wash position in the wash station 158. The photometer means 46 includes eight photometer units equi-angularly spaced, each of which make one observation each cycle or dwell period of each cuvette to result in one hundered observations or absorbance readings at each wavelength of interest between the position 18' and the wash stand 158. The observations at each wavelength of interest are utilized to determine the rate of reaction or the end point of the reaction or both. If desired one or more reactions may be observed more frequently at the same wavelength in the testing sequence. In that case two or more of the photometer units would utilize the same wavelength and there would be two hundred observations or readings at the wavelength of interest during the same ten minute period of the reaction.

As previously discussed, each of the photometer units is actually reading each of the cuvettes each time it passes by whether there is a complete reaction mixture in the cuvette or not. Further, each of these readings such as in the wash station or the cuvette blanks may have a separate utility in determining whether or not the analyzer 10 is operating correctly.

The sample tray or disc 14 may be of a molded type having the cavities 20 and 24 molded therein. The outer ring may have sixty-four or ninty-six cavities while the inner ring conveniently may have eight cavities. The ninety-six regular or normal samples will be in three circular rows (two rows if sixty-four) with thirty-two numbered cavities or positions in each row. The analyzer 10 matches each position or sample with each patient throughout the series of tests to correlate the patient with the results of each test on the patient's sample. The sample volume selected by the variable syringe 82 is from two to twenty microliters in incremental values of 2, 4, 6, 8, 10 and 20 microliters.

The throughput of the machine is six hundred results per hour. With one test on each patient sample, there might be fifty patient profiles per hour with eleven tests on each patient sample and a blank or control every twelveth cuvette. The first reagent syringe 134 has incremental values of 100, 200, 300, 400 and 500 microliters. The second reagent syringe 152 has incremental values of 20, 40, 60, 80 and 100 microliters.

For a reaction from the position 18', with a single reagent added at position 18'', there is an observation time of nine minutes and fifty-four seconds from the position 18'' to the initial position in the wash station 158. For a reaction with a second reagent added at the position 18''' there is an observation time or time of reaction monitoring of seven minutes and fifty-four seconds from the position 18''' to the initial position of the wash station 158. The range of wavelengths of the photometer units is from three hundred forty nanometers to seven hundred nanometers which could be broader if desired. The minimum volume of sample aliquot and diluent placed into the cuvette 18 is one hundred microliters. The blank readings are obtained on each reagent initially and each cuvette and each sample and reaction mixture during each sequence. All possible eight wavelengths are utilized to establish the initial blanking values for the analyzer 10 and to observe each cuvette.

Many modifications and variations of the present invention are possible in light of the above teachings. For example, a single dispensing arm could be utilized for all functions, but the dwell period would then be eighteen seconds for each operational cycle in the glucose example. Further, a single reagent dispensing arm could be used in addition to the sample arm in which case the dwell period would be twelve seconds for each operational cycle in the glucose example. The trays 14 and 16 could be replaced with other types of movable arrays such as rectangular or belt type drives, the only criterion being that the pick up position would have to be on the arc of the dispensing arm probe. The direction of the rotation of the arm could be changed such as moving the arm 28 to the right of the tray 14. The aspiration of the same aliquots and their respective reagents also could be done with a level control probe with the tabs 78 and 122 only being utilized to determine that the probes are in the down position in the cuvettes 18.

The second reagents dispensed at the position 18''', preferably should be those which do not need as much reaction and observation time as those dispensed at the position 18''. The second reagents may be added in combination with the first reagents or the first and second reagents may be added to separate sample aliquots to form separate reagent mixtures. The situation also may arise where the number of reagent positions in the first reagent ring are insufficient for a particular reagent volume, in which case the second reagent ring would contain additional containers of the same reagent. This situation would arise where numerous tests are programmed to utilize the same reagent. The syringe 170 for the wash stand 160 could be eliminated by utilizing the vacuum developed by the pump 206. It is, therefore, to be understood that within the scope of the appended claims, the invention may be practiced otherwise than as specifically described.

What is claimed and desired to be secured by Letters Patent of the United States is:

1. A method of testing samples comprising:
   A. arranging a first plurality of samples into a sequence of sample positions for sequential testing;
   B. moving a predetermined one of said sequenced sample positions to a first sample pick up location;
   C. picking up at least a first sample aliquot in the first sample pick up location and dispensing the aliquot into a reaction vessel;
   D. moving at least one predetermined reagent position from one of a plurality of first reagent positions containing a reagent to a first reagent pick up location;
   E. picking up a predetermined aliquot of said reagent in the first reagent pick up location and dispensing said reagent aliquot into said reaction vessel;
   F. testing at least the resulting combination of sample and reagent aliquots in said reaction vessel; and
   G. interrupting said sequential testing by picking up an aliquot of an auxiliary sample from a second pick up location separated from said sequenced sample positions and dispensing said auxiliary aliquot into a reaction vessel.

2. A method of testing samples as claimed in claim 1 including:
   repeating said testing sequence for successive aliquots of said sequenced samples; and
   picking up an auxiliary control aliquot in a predetermined frequency of repeating step G.

3. A method of testing samples as claimed in claim 1 further including:
   providing a plurality of auxiliary sample positions containing said auxiliary samples and moving a predetermined one of said auxiliary sample positions to said second sample pick up location prior to picking up the aliquot of said auxiliary sample.

4. A method of testing samples as claimed in claim 3 further including:
   locating the positions of each of said sequenced samples, said emergency samples and said controls in an annular array and independently rotating predetermined ones of the locations to said first and second sample pick up locations prior to picking up the aliquots at said pick up positions.

5. A method of testing samples as claimed in claim 3 further including:
   locating said plurality of sequenced sample positions in a plurality of annular rings with said first sample pick up location being located on an arc having a common radius with the second sample pick up location, said first sample pick up location including a separate pick up position on each of said rings.

6. A method of testing samples as claimed in claim 1 further including:
   moving said reagent aliquot from said reagent pick up location and dispensing said aliquot into said reaction vessel at a separate reagent dispensing position spaced from said reagent pick up location.

7. A method of testing samples as claimed in claim 1 further including:
   moving said sample sequenced aliquot from said first sample pick up location and dispensing said aliquot into said reaction vessel at a separate sample dispensing position spaced from said pick up location.

8. A method of testing samples as claimed in claim 7 further including:
   moving said reaction vessel from said sample dispensing position to a reagent dispensing position prior to dispensing said reagent aliquot, and
   moving said reagent aliquot from said reagent pick up location to said reagent dispensing position to dispense said reagent aliquot into said reaction vessel.

9. A method of testing samples as claimed in claim 1 further including:
   moving at least one predetermined second reagent position from one of a plurality of second reagent positions containing second reagents to a second reagent pick up location, picking up a predetermined aliquot of said second reagent in said second reagent pick up location and dispensing said second reagent aliquot into said reaction vessel prior to testing at least said combined sample and reagent aliquots in said reaction vessel.

10. A method of testing samples as claimed in claim 9 further including:
    moving said reagent aliquots from said reagent pick up locations and dispensing the aliquots into said reaction vessel at a separate reagent dispensing position spaced from said pick up locations.

11. A method of testing samples as claimed in claim 10 further including:
    moving said sample aliquot from said first sample pick up location and dispensing said aliquot into said reaction vessel at a separate sample dispensing position spaced from said pick up location.

12. A method of testing samples as claimed in claim 11 further including:
    moving said reaction vessel from said sample dispensing position to a first reagent dispensing position prior to dispensing said reagent aliquot;
    moving said reagent aliquot from said first reagent pick up location to said first reagent dispensing position to dispense said reagent aliquot into said reaction vessel;
    moving said reaction vessel from said first reagent dispensing position to a second reagent dispensing position prior to dispensing said second reagent aliquot, and
    moving said second reagent aliquot from said second reagent pick up location to said second reagent dispensing position to dispense said second reagent aliquot into said reaction vessel.

13. A method of testing samples as claimed in claim 8 further including:
    providing a plurality of reaction vessels in an array and sequentially moving them to and removing them from said sample and reagent dispensing positions.

14. A method of testing samples as claimed in claim 13 further including:
    identifying the position of each said reaction vessel in said array.

15. A method of testing samples as claimed in claim 13 further including:
    locating said reaction vessels in an annular array and rotating them to and from said dispensing locations.

16. A method of testing samples as claimed in claim 15 further including:
    indexing said array in said annular path and scanning said array with photometer means in a predetermined sequence for a period of time to determine at least one of a reaction rate or an end point or equilibrium condition of at least one of said combined sample and reagent aliquots in said reaction vessels.

17. A method of testing samples as claimed in claim 16 further including:
    identifying the position of at least one reaction vessel in said array by said photometer means to determine which reaction vessel is being scanned by said photometer means.

18. A method of testing samples as claimed in claim 17 further including:
    scanning said reaction vessels with a plurality of photometers in said photometer means, each of said photometers having a predetermined angular orientation and coordinating the position of at least one of said reaction vessels with at least one of said dispensing locations to determine the reaction vessel being scanned by each photometer.

19. A method of testing samples as claimed in claim 1 further including:
    diluting said sample aliquot with a predetermined quantity of diluent prior to said testing.

20. A method of testing samples as claimed in claim 1 further including:

picking up and dispensing said sample aliquots with a probe rotated about a fixed point and movable downwardly into said pick up positions and said reaction vessels; and simultaneously washing said probe externally and internally after dispensing each of said sample aliquots.

21. A method of testing samples as claimed in claim 1 further including:

substantially simultaneously picking up said sample aliquot and said reagent aliquot and dispensing said sample aliquot and said reagent aliquot into separate reaction vessels at separate locations; and testing at least said combined sample and reagent aliquots in said vessels by observing the changes in optical absorbance of said aliquots.

22. A method of testing samples comprising:
A. moving a predetermined sample position from one of a plurality of sample positions containing a sample to a first sample pick up location;
B. picking up at least a first sample aliquot in the first sample pick up location and dispensing the aliquot into a reaction vessel;
C. moving at least one predetermined reagent position from one of a plurality of first reagent positions containing a reagent to a first reagent pick up location;
D. picking up a predetermined aliquot of said reagent in the first reagent pick up location and dispensing said reagent aliquot into said reaction vessel;
E. testing at least the resulting combination of sample and reagent aliquots in said reaction vessel;
F. moving said reaction vessel to a separate wash position after said combination of sample and reagent aliquots has been tested; and
G. evacuating said combination of sample and reagent aliquots from said reaction vessel, washing said reaction vessel, adding a blanking solution to said vessel and thereafter testing said vessel to determine whether said vessel is clean prior to reusing said reaction vessel.

23. A method of testing samples as claimed in claim 22, wherein said testing in steps E and G is performed with photometer means at a predetermined wavelength for each test; and further including:

repeating steps A through G wherein said testing of said reaction vessel and blanking solution in step G is performed at the same wavelength of the previously completed test in step E; comparing the test result in step G with the result using said same test wavelength in the previous cleaning test in step G to determine whether said vessel is clean; and thereafter if said vessel is clean, testing said vessel containing said blanking solution at the new test wavelength to be utilized in the next test for the next sample and reagent aliquots to be introduced into the reaction vessel.

24. A method of testing samples as claimed in claim 23 further including:

evacuating said blanking solution from said reaction vessel;

drying said empty reaction vessel;

testing said empty reaction vessel again at said previous test wavelength to see if said reaction vessel has been evacuated; and if said reaction vessel has been evacuated, testing said reaction vessel at said new test wavelength prior to adding said new sample and reagent aliquots.

25. A method of testing samples as claimed in claim 24 further including:

dispensing said new sample aliquot into said clean reaction vessel only if it passes said cleanliness test and eliminating said reaction vessel from the testing sequence if it fails said test.

26. A method of testing samples comprising:
A. moving a predetermined sample position from one of a plurality of sample positions containing a sample to a first sample pick up location;
B. picking up at least a first sample aliquot in the first sample pick up location and dispensing the aliquot into a reaction vessel;
C. moving at least one predetermined reagent position from one of a plurality of first reagent positions containing a reagent to a first reagent pick up location;
D. picking up a predetermined aliquot of said reagent in the first reagent pick up location and dispensing said reagent aliquot into said reaction vessel;
E. testing at least the resulting combination of sample and reagent aliquots in said reaction vessel; and
F. testing said reagent aliquot in said reaction vessel and evacuating said aliquot prior to adding said sample aliquot to determine the test value of the reagent aliquot in said reaction vessel to form a reagent blank.

27. A method of testing samples as claimed in claim 26 further including:

testing said sample aliquots dispensed in each said reaction vessel to determine a sample blank prior to adding said reagent aliquot to said reaction vessel; for testing said combined sample and reagent aliquots in said reaction vessel until said reaction reaches equilibrium, and computing the end point or equilibrium value by subtracting the known separate reagent and sample blanking values from the tested combination equilibrium value.

28. A sample testing apparatus comprising:
A. means for arranging a first plurality of samples into a sequence of sample positions for sequential testing;
B. means for moving a predetermined one of said sequenced sample positions to a first sample pick up location;
C. means for picking up at least a first sample aliquot in the first sample pick up location and dispensing the aliquot into a reaction vessel;
D. means for moving at least one predetermined reagent position from one of a plurality of first reagent positions containing a reagent to a first reagent pick up location;
E. means for picking up a predetermined aliquot of said reagent in the first reagent pick up location and dispensing said reagent aliquot into said reaction vessel;
F. means for testing at least the resulting combination of sample and reagent aliquots in said reaction vessel; and
G. means for interrupting said sequential testing by picking up an aliquot of an auxiliary sample from a second pick up location separated from said sequenced sample positions and dispensing said auxiliary aliquot into a reaction vessel.

29. A sample testing apparatus as claimed in claim 28 including:
means for repeating said testing sequence for successive aliquots of said sequenced samples; and
means for picking up an auxiliary control aliquot in a predetermined frequency of a repeating step G.

30. A sample testing apparatus as claimed in claim 28 further including:
a plurality of auxiliary sample positions for containing said auxiliary samples and means for moving a predetermined one of said auxiliary sample positions to said second sample pick up location prior to picking up the aliquot of said auxiliary sample.

31. A sample testing apparatus as claimed in claim 30 further including:
rotatable means including the positions of each of said sequenced samples, said emergency samples and said controls arranged in an annular array thereon and means for independently rotating predetermined ones of the positions to said first and second sample pick up locations prior to picking up the aliquots at said pick up locations.

32. A sample testing apparatus as claimed in claim 30 further including:
a rotatable tray having said plurality of sequenced sample positions in a plurality of annular rings thereon with said first sample pick up location being located on an arc having a common radius with the second sample pick up location, said first sample pick up location including a separate pick up position on each of said rings.

33. A sample testing apparatus as claimed in claim 28 wherein said reagent pick up means include:
means for moving said reagent aliquot from said reagent pick up location and dispensing said aliquot into said reaction vessel at a separate reagent dispensing position spaced from said reagent pick up location.

34. A sample testing apparatus as claimed in claim 28 wherein said sample pick up means include:
means for moving said sequenced aliquot from said first sample pick up location and dispensing said aliquot into said reaction vessel at a separate sample dispensing position spaced from said pick up location.

35. A sample testing apparatus as claimed in claim 34 further including:
means for moving said reaction vessel from said sample dispensing position to a reagent dispensing position prior to dispensing said reagent aliquot, and
said reagent pick up means include means for moving said reagent aliquot from said reagent pick up location to said reagent dispensing position to dispense said reagent aliquot into said reaction vessel.

36. A sample testing apparatus as claimed in claim 28 further including:
means for moving at least one predetermined second reagent position from one of a plurality of second reagent positions containing second reagents to a second reagent pick up location, means for picking up a predetermined aliquot of said second reagent in said second reagent pick up location and dispensing said second reagent aliquot into said reaction vessel.

37. A sample testing apparatus as claimed in claim 36 wherein said reagent pick up means include:
means for moving said reagent aliquots from said reagent pick up locations and dispensing the aliquots into said reaction vessel at a separate reagent dispensing position spaced from said pick up locations.

38. A sample testing apparatus as claimed in claim 37 wherein said sample pick up means include:
means for moving said sample aliquot from said first sample pick up location and dispensing said aliquot into said reaction vessel at a separate sample dispensing position spaced from said pick up location.

39. A sample testing apparatus as claimed in claim 38 further including:
means for moving said reaction vessel from said sample dispensing position to a first reagent dispensing position prior to dispensing said reagent aliquot;
said reagent pick up means include means for moving said reagent aliquot from said first reagent pick up location to said first reagent dispensing position to dispense said reagent aliquot into said reaction vessel;
means for moving said reaction vessel from said first reagent dispensing position to a second reagent dispensing position prior to dispensing said second reagent aliquot, and
said means for moving said second reagent aliquots include means for moving said second reagent aliquot from said second reagent pick up location to said second reagent dispensing position to dispense said second reagent aliquot into said reaction vessel.

40. A sample testing apparatus as claimed in claim 35 further including:
a reaction vessel structure having a plurality of reaction vessels in an array and means for sequentially moving them to and removing them from said sample and reagent dispensing positions.

41. A sample testing apparatus as claimed in claim 40 further including:
means for identifying the position of each said reaction vessel in said array.

42. A sample testing apparatus as claimed in claim 40 wherein:
said reaction vessels are located in said structure in an annular array and said sequential moving means include means for rotating them to and from said dispensing locations.

43. A sample testing apparatus as claimed in claim 42 further including:
means for indexing said array in said annular path and means for scanning said array with photometer means in a predetermined sequence for a period of time to determine at least one of a reaction rate or an end point or equilibrium condition of at least one of said combined sample and reagent aliquots in said reaction vessels.

44. A sample testing apparatus as claimed in claim 43 further including:
means for identifying the position of at least one reaction vessel in said array by said photometer means to determine which reaction vessel is being scanned by said photometer means.

45. A sample testing apparatus as claimed in claim 44 further including:
a plurality of photometers in said photometer means, and scanning said reaction vessels with said plurality of photometers, each of said photometers having a predetermined angular orientation and means for coordinating the position of at least one of said reaction vessels with at least one of said dispensing locations to determine the reaction vessel being scanned by each photometer.

46. A sample testing apparatus as claimed in claim 28 further including:
   means for diluting said sample aliquot with a predetermined quantity of diluent prior to said testing.

47. A sample testing apparatus as claimed in claim 28 wherein said sample pick up means include:
   probe means for picking up and dispensing said sample aliquots including a probe rotated about a fixed point and movable downwardly into said pick up positions and said reaction vessels; and
   means for simultaneously washing said probe externally and internally after dispensing each of said sample aliquots.

48. A sample testing apparatus as claimed in claim 28 further including:
   means for substantially simultaneously picking up said sample aliquot and said reagent aliquot and dispensing said sample aliquot and said reagent aliquot into separate reaction vessels at separate locations; and
   means for testing at least said combined sample and reagent aliquots in said vessels by observing the changes in optical absorbance of said aliquots.

49. A sample testing apparatus comprising:
   A. means for moving a predetermined sample position from one of a plurality of sample positions containing a sample to a first sample pick up location
   B. means for picking up at least a first sample aliquot in the first sample pick up location and dispensing the aliquot into a reaction vessel;
   C. means for moving at least one predetermined reagent position from one of a plurality of first reagent positions containing a reagent to a first reagent pick up location;
   D. means for picking up a predetermined aliquot of said reagent in the first reagent pick up location and dispensing said reagent aliquot into said reaction vessel;
   E. means for testing at least the resulting combination of sample and reagent aliquots in said reaction vessel;
   F. means for moving said reaction vessel to a separate wash position after said combination of sample and reagent aliquots has been tested; and
   G. means for evacuating said combination of sample and reagent aliquots from said reaction vessel, means for washing said reaction vessel, means for adding a blanking solution to said vessel and thereafter testing said vessel to determine whether said vessel is clean prior to reusing said reaction vessel.

50. A sample testing apparatus as claimed in claim 49 wherein:
   said testing means includes photometer means operating at a variable wavelength for each test;
   said photometer means testing said reaction vessel and blanking solution at the wavelength of the previously completed test of said combination and means for comparing the result of said blanking solution test with the result using the same test wavelength in the previous blanking solution test to determine whether said vessel is clean.

51. A sample testing apparatus as claimed in claim 50 further including:
   means for evacuating said blanking solution from said reaction vessel;
   means for drying said empty reaction vessel;
   said photometer means testing said empty reaction vessel again at said previous test wavelength to see if said reaction vessel has been evacuated.

52. A sample testing apparatus as claimed in claim 51 further including:
   means for eliminating said reaction vessel from the testing sequence if it fails said cleanliness test and dispensing said new sample aliquot into said clean reaction vessel only if it passes said cleanliness test.

53. A sample testing apparatus comprising:
   A. means for moving a predetermined sample position from one of a plurality of sample positions containing a sample to a first sample pick up location;
   B. means for picking up at least a first sample aliquot in the first sample pick up location and dispensing the aliquot into a reaction vessel;
   C. means for moving at least one predetermined reagent position from one of a plurality of first reagent positions containing a reagent to a first reagent pick up location;
   D. means for picking up a predetermined aliquot of said reagent in the first reagent pick up location and dispensing said reagent aliquot into said reaction vessel;
   E. means for testing at least the resulting combination of sample and reagent aliquots in said reaction vessel; and
   F. means for testing said reagent aliquot in said reaction vessel and evacuating said aliquot prior to adding said sample aliquot to determine the test value of the reagent aliquot in said reaction vessel to form a reaction blank.

54. A sample testing apparatus as claimed in claim 53 further including:
   means for testing said sample aliquots dispensed in each said reaction vessel to determine a sample blank prior to adding said reagent aliquot to said reaction vessel;
   means for testing said combined sample and reagent aliquots in said reaction vessel until said reaction reaches equilibrium; and
   means for computing the end point or equilibrium value by subtracting the known separate reagent and sample blanking values from the tested combination equilibrium value.

55. A method of testing samples as claimed in claim 22, 23, 24, 25, 26, or 27, wherein said testing is performed by scanning said reaction vessels with a plurality of photometers, and coordinating the position of at least one of said reaction vessels with at least one dispensing location to determine the reaction vessel being scanned by each photometer.

56. A sample testing apparatus as claimed in claim 49, 50, 51, 52, 53 or 54, wherein said testing means includes a plurality of photometers for scanning said reaction vessels.

57. A method for continuous testing of samples comprising:
   (A) rotating a plurality of reaction vessel in stepwise manner on an axis;
   (B) rotating a plurality of photometers on said axis at higher speed than the stepwise rotation of said reaction vessels;

(C) sequentially picking up sample aliquots from a sequence of said samples arranged for a program of testing and sequentially depositing said samples in said stepped reaction vessels;

(D) picking up predetermined reagent aliquots from a plurality of reagent positions and dispensing said reagent aliquots into said reaction vessels;

(E) scanning the resulting combinations of sample and reagent aliquots in said reaction vessels with said plurality of photometers, and processing the results of said photometric scanning to determine the reaction rate or end point produced by combination of said sample and reagent aliquots;

(F) interrupting said sequential program of testing by picking up an aliquot of an auxiliary sample from a position separated from said arrangement of sequenced samples and dispensing said auxiliary aliquot into a reaction vessel; and thereafter, (G) continuing said scanning of said vessels including said vessel containing said auxiliary sample aliquot.

* * * * *